United States Patent [19]

Johnson et al.

[11] 4,038,065

[45] July 26, 1977

[54] 1-ALKYLPYRID-2-ONE

[75] Inventors: Wayne O. Johnson, Warminster; Michael C. Seidel, Chalfont; Harlow L. Warner, Hatboro, all of Pa.

[73] Assignee: Rohm and Haas Company, Philadelphia, Pa.

[21] Appl. No.: 513,987

[22] Filed: Oct. 11, 1974

[51] Int. Cl.$^2$ ............... C07D 213/80; A01N 9/22
[52] U.S. Cl. ................................. 71/76; 71/94; 260/294.9; 260/295.5 R; 260/295.5 A
[58] Field of Search ............. 260/295.5 R, 295.5 A; 71/94

[56] References Cited

U.S. PATENT DOCUMENTS 3,576,814   4/1971   Seidel et al. ............... 260/295.5 R

OTHER PUBLICATIONS

Sorm et al., "Chem. Abstracts", vol. 44, p. 1505g.
Santararo, "Chem. Abstracts", v. 50, (1956), p. 12145e.
Tanaka et al., "Chem. Abstracts", v. 67, (1967), No. 43650n.
Chambers et al., "Chem. Abstracts", v. 66, (1967), No. 84597y.
Moehrle et al., "Chem. Abstracts", v. 75, (1971), No. 35630f.
Ueda, "Chem. Abstracts", v. 46, (1952), p. 4541e.
Holman et al., "Chem. Abstracts", v. 44, (1950), p. 2985h.
Hardegger et al., "Chem. Abstracts", v. 50, (1956), pp. 13920–13921.
Robinson et al., "Chem. Abstracts", v. 61, (1964), p. 16364a.
Agbalyan et al., "Chem. Abstracts", v. 70, (1969), No. 105906y.
Ganguly et al., "Chem. Abstracts", v. 73, (1970), No. 77440h.

*Primary Examiner*—Henry R. Jiles
*Assistant Examiner*—R. W. Ramsuer
*Attorney, Agent, or Firm*—George W. F. Simmons; William E. Lambert, III; Bernard J. Burns

[57] ABSTRACT

Novel compounds belonging to the class of 3-carboxy (or the physiologically acceptable salts thereof), 3-carbalkoxy, and 3-carbamoyl-1-alkyl-4,6-disubstituted pyrid-2-ones. These compounds possess biological activity and in particular are gametocides and plant growth regulators. Novel 3-cyano-1-alkyl-4,6-disubstituted pyrid-2-ones are also disclosed as intermediates.

7 Claims, No Drawings

1-ALKYLPYRID-2-ONE

SUMMARY OF THE INVENTION

This invention is concerned with novel organic compounds belonging to the general class of 1-alkylpyrid-2-ones. It also relates to the biological activity of these structures. In particular they are useful as plant growth regulators and gametocidal agents.

The cereal grains, such as corn, wheat, rice, and barley are among the major food crops throughout the world. This importance has led to extensive research to improve both the productivity and food value of these crops. One of the most important approaches taken to improve the quality of the cereal grains has been hybridization. While hybridization has been an effective technique for some crops, most notably corn, there have been a number of problems with present techniques. For example, corn hybridization requires time-consuming hand detasseling or inefficient mechanical detasseling, possibly injuring the corn plant. Corn, barley, and wheat hybridization by means of cytoplasmic male sterile varieties can only be done with a limited genetic base, requiring a maintainer line and a restorer line. Furthermore, cytoplasmic male sterile techniques with barley and wheat necessitate a highly sophisticated approach to deal with the genetic complexities of these crops, and great success has not yet been reached in developing a suitable approach. Since the induction of selective male sterility by chemical means would obviate many of the problems confronting the present hybridization techniques, new compounds which produce the desired sterility would be extremely desirable in dependably and economically supplying the male sterile plants needed for hybridization.

A new class of compounds has now been found which can be used to induce plant growth regulatory activity in cereal grains. The compounds of the invention are 1-alkylpyrid-2-ones which may be depicted by formula (I)

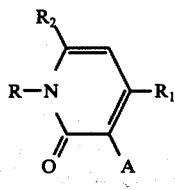

(I)

wherein:
A is a cyano group or

wherein Y is a halogen atom an $NH_2$, OH, or $(C_1-C_7)$ alkoxy group;
R is a $(C_1-C_{12})$ alkyl group; and
$R_1$ and $R_2$ are a hydrogen atom a methyl or ethyl group.

In this invention an alkyl group can be branched or straight chained. Any suitable physiologically acceptable basic addition salt of the carboxylic acids of this invention can be utilized. Typical salts can be sodium, potassium, ammonium, dimethyl ammonium, diethylammonium, etc. The preferred compounds of this invention are where A is carboxyl and the physiologically acceptable salts thereof. The more preferred compounds of this invention are where $R_1$ and $R_2$ are methyl while A is carboxyl and the physiologically acceptable salts thereof.

Typical compounds within the scope of this invention include:

1-methyl-3-carboxy-4,6-dimethylpyrid-2-one
1-isobutyl-3-carboxy-4,6-dimethylpyrid-2-one
1-(n-hexyl)-3-carboxy-4,6-dimethylpyrid-2-one
1-(2-ethylhexyl)-3-carboxy-4,6-dimethylpyrid-2-one
1-(n-decyl)-3-carboxy-4,6-dimethylpyrid-2-one
1-isopropyl-3-carboxypyrid-2-one
1-(t-butyl)-3-carboxy-pyrid-2-one
1-(n-heptyl)-3-carboxy-pyrid-2-one
1-(2-ethylhexyl)-3-carboxy-pyrid-2-one
1-(2-ethylhexyl)-3-carboxyl-6-methylpyrid-2-one
1-propyl-3-carboxy-6-methylpyrid-2-one
1-butyl-3-carboxy-6-methylpyrid-2-one
1-isopentyl-3-carboxy-6-methylpyrid-2-one
1-(2-methylhexyl)-3-carboxy-6-methylpyrid-2-one
1-(n-octyl)-3-carboxy-6-methylpyrid-2-one
1-(2-ethylnonyl)-3-carboxy-6-methylpyrid-2-one and salts thereof
1-methyl-3-cyano-4,6-dimethylpyrid-2-one
1-isobutyl-3-cyano-4,6-dimethylpyrid-2-one
1-(n-hexyl)-3-cyano-4,6-dimethylpyrid-2-one
1-(2-ethylhexyl)-3-carbomethoxy-4,6-dimethylpyrid-2-one
1-methyl-3-carbamoyl-4,6-dimethylpyrid-2-one
1-isobutyl-3-carbamoyl-4,6-dimethylpyrid-2-one
1-(n-hexyl)-3-carbamoyl-4,6-dimethylpyrid-2-one
1-(2-ethylhexyl)-3-carbamoyl-4,6-dimethylpyrid-2-one
1-(n-decyl)-3-carbamoyl-4,6-dimethylpyrid-2-one The compounds of this invention may be prepared by the following reaction scheme:

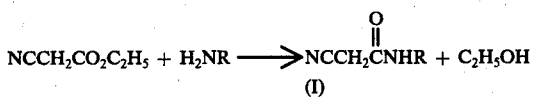

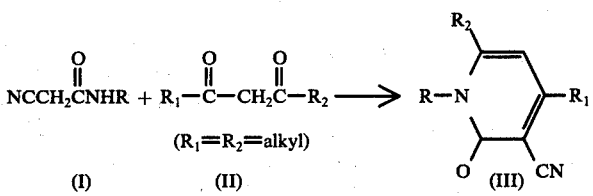

N-alkyl cyanoacetamides (Formula I) are known compounds which may be made by heating ethyl cyanoacetate with the appropriate amine usually under neat conditions, and removing the ethanol as formed according to the above reaction scheme. This is usually a facile reaction in the temperature range of 25°–160° C. The end of the reaction is judged when the removal of ethanol is essentially completed. The reaction product may be used without further purification. Refer to Piccinini et al., *Chemishes Zentralblatt*, 78,335 (1907).

The beta-diketones (Formula II) may be made by the general methods described by J. T. Adams et al., *J. Chem. Soc.* 66,1220 (1944) and A. W. Johnson et al., *Organic Synthesis* 42,75 (1962). Pentane-2,4-dione is a product of commerce.

The 1-alkyl-3-cyanopyrid-2-ones (Formula III) may be prepared by condensation of beta-diketones (Formula II) with N-alkyl cyanoacetamides (Formula I) in the presence of a basic catalyst.

In the condensation of beta-diketone with the N-alkyl acetamide equimolar amounts of the two reactants are normally used, although excesses of either reagent are permissable. In some instance, it may be expendient to use an excess of the beta-diketone.

The condensation of the beta-diketone with an N-alkyl-cyanoacetamide is preferably carried out in the presence of a solvent. Suitable solvents include alcohols, ethers, aliphatic, hydrocarbons, dimethylformamide, dimethyl sulfoxide and carbon tetrachloride. The preferred solvents are the alcohols such as methanol, ethanol, ispropanol and monethers of ethylene glycol. Heat is sometimes required for the condensation and this is usually obtained at the reflux temperature of the solvent used. Temperatures in the range of about 25° to about 150° C. are suitable.

The condensation of the beta-diketone with an N-alkyl-cyanoacetamide is catalyzed by basic catalysts. Typical catalysts include inorganic bases, amines and quaternary ammonium hydroxides. Amine catalysts are preferred and good results can be obtained with piperidine, pyridine, diethylamine and triethylamine for example. General conditions for this type of condensation are reviewed in "Heterocyclic Compounds," edited by A. Weissberger, Interscience Publishers, 1962, in Part III on "Pyridinols and Pyridones," pages 525–531.

The 1-alkyl-3-cyano-pyrid-2-ones can also be prepared by the general method described in the above cited book "Heterocyclic Compounds" on page 596. This consists of quaternizing a 3-cyanopyridine with an iodalkane in a solvent having a high dielectric constant, such as acetonitrile, and oxidizing the resulting pyridinium salt with alkaline potassium ferricyanide to the corresponding α-pyridone. The reaction may be depicted as follows:

The 1-alkyl-3-cyano-4,6-dimethylpyrid-2-ones may also be prepared by a ring-closure procedure generally described in the above cited book, "Heterocyclic Compounds" on page 551. The reaction may be depicted for the 3-methoxycarbonyl compounds as follows:

The compounds of (Formula V) may be converted to the corresponding carboxy compounds or their water-soluble salts by standard hydrolytic procedures.

The hydrolysis of 1-alkyl-3-cyanopyrid-2-ones may proceed to either the amide (Formula IV) or the acid (Formula V) under acidic conditions. Aqueous organic and mineral acids are formic, acetic, hydrochloric, hydrobromic, sulfuric and phosphoric. The temperature requirements for the hydrolysis are such that the temperature must be high enough to allow the hydrolysis to proceed but not sufficiently high to cause decarboxylation. This is normally in the range of 50° to 150° C., with a preferred range of 80° to 120° C. The cyano compounds of (Formula III) can be converted to the carbamoyl derivatives of (Formula IV) by hydrolysis with hydrogen peroxide in dilute base or by other methods known in the art. The carbamoyl derivatives can be hydrolyzed to the free acids of (Formula V) by means of nitrous acid or by other hydrolytic procedures well known in the chemical art.

The 1-alkyl-3-carboxypyrid-2-ones may be prepared by the following reaction scheme:

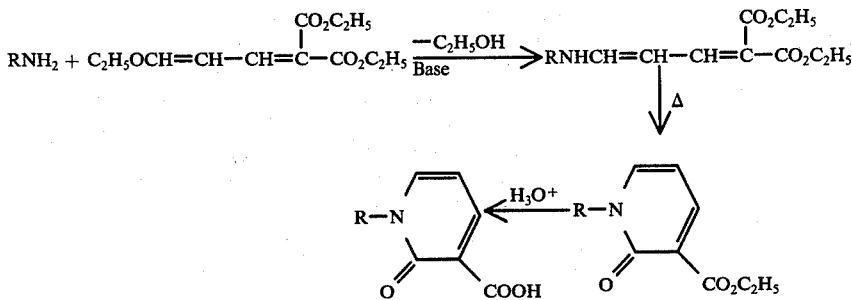

Diethyl 2-(5-ethoxyalkylidine) malonate is heated with the appropriate amine usually under neat conditions, and the ethanol is removed as formed. The temperature range for the reaction is from about 65° to 185° C. The end of the reaction is judged when the removal of ethanol is essentially completed. The ester so formed is purified via recrystallization and hydrolyzed under acidic conditions.

The 1-alkyl-3-carboxy-6-methylpyrid-2-ones may be prepared by the following reaction scheme:

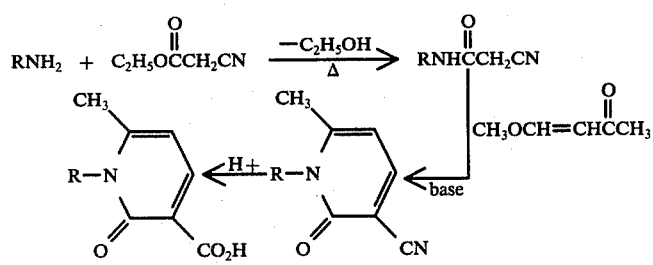

The N-alkyl cyanoacetamide is prepared as above. The reaction of the N-alkyl cyanoacetamide with 4-methoxy-3-butene-2-one takes place at reflux in the presence of a base and an appropriate solvent such as methyl cellosolve, n-butanol, and the like. The 1-alkyl-3-cyano-6-methylpyrid-2-one is hydrolyzed as above to the corresponding 1-alkyl-3-carboxy-6-methylpyrid-2-one.

The acids of Formula V are readily converted to derivatives. For example, direct esterification with alcohols gives esters and reaction with halogenating agents such as oxalyl chloride, thionyl chloride or bromide and phosphorus pentachloride gives the acid halides. The acid halides can in turn be converted to esters, amides, anilides and other common derivatives by standard procedures.

The following examples are to be construed as illustrations of the preparation of the compounds of the invention and not as limitations thereof.

EXAMPLE I

Preparation of 1-methyl-3-carboxy-4,6-dimethylpyrid-2-one a. N-methyl cyanoacetamide Ethyl cyanoacetate (226 g., 2.0 mole) and a 33% aqueous methylamine solution (400 ml.) is stirred at room temperature for 3 hours. The water is removed under reduced pressure to give N-methylcyanoacetamide, 200 g. (100% yield), mp. 84°–91° C.

b. 1-methyl-3-cyano-4,6-dimethylpyrid-2-one

N-methyl cyanoacetamide (113 g., 1.15 mole), 2,4-pentanedione (115 g., 1.15 mole), piperidine (11.5 ml.) and anhydrous ethanol (250 ml.) are refluxed with stirring for 3 hours. The mixture is allowed to stand overnight at room temperature and the white crystalline precipitate is collected by filtration to give 1-methyl-3-cyano-4,6-dimethylpyrid-2-one, 144 g. (77.4% yield), mp. 202°–205° C.

c. 1-methyl-3-carboxy-4,6-dimethylpyrid-2-one

To a stirred mixture of 1-methyl-3-cyano-4,6-dimethyl-pyrid-2-one (144 g., 0.89 mole) and 110 ml. of water is slowly added concentrated sulfuric acid (220 ml.) and the solution is heated on a steam bath for 24 hours. The solution is poured into 6 liters of water, cooled, and the resulting precipitate is collected by filtration and dried in a vacuum oven to give 1-methyl-3-carboxy-4,6-dimethylpyrid-2-one, 97 g. (60% yield), mp. 200°–204° C.

Anal. Calc'd for $C_9H_{11}NO_3$: C, 59.65; H, 6.12; N, 7.73. Found: C, 59.54; H, 5.88; N, 7.60.

EXAMPLE II

Preparation of 1-isobutyl-3-carboxy-4,6-dimethylpyrid-2-one a. N-isobutyl cyanoacetamide Ethyl cyanoacetate (113 g., 1.0 mole) and isobutylamine (73 g., 1.0 mole) were refluxed with stirring for 2 hours to give N-isobutyl cyanoacetamide.

b. 1-isobutyl-3-cyano-4,6-dimethylpyrid-2-one

To the above solution is added anhydrous ethanol (250 ml.), 2,4-pentanedione (100 g., 1.0 mole) and piperidine (10 ml.) and the resulting solution is then refluxed with stirring for 3.5 hours. The reaction mixture is concentrated under reduced pressure to remove the ethanol, then cooled in an ice bath and the yellow crystals are filtered and dried in vacuo to give 49.8 g. (24.3% yield) of 1-isobutyl-3-cyano-4,6-dimethylpyrid-2-one, mp. 126.5°–128.5° C.

c. 1-isobutyl-3-carboxy-4,6-dimethylpyrid-2-one

To a mixture of 1-isobutyl-3-cyano-4,6-dimethylpyrid-2-one (99.8 g., 0.489 mole) and 100 ml. of water is slowly added, with stirring, concentrated sulfuric acid (200 ml.) When the addition of complete the reaction mixture is heated on a steam bath for 24 hours. The solution is then poured into a sodium hydroxide solution and filtered. The alkaline filtrate is acidified and the resulting solid is then collected by filtration to give 1-isobutyl-3-carboxy-4,6-dimethylpyrid-2-one, 44.5 g. (40.6% yield), mp 93°–95° C.

Anal. Calc'd for $C_{12}H_{17}NO_3$: C, 64.54; H, 7.68; N, 6.27. Found: C, 64.55; H, 7.72; N, 6.28.

EXAMPLE III

Preparation 1-(n-hexyl)-3-carboxy-4,6-dimethylpyrid-2-one a. N-(n-hexyl)-cyanoacetamide Ethyl cyanoacetate (113 g., 1.0 mole), n-hexylamine (101 g., 1.0 mole) and methyl cellosolve (200 ml.) are refluxed with stirring for 1.5 hours and the solvent is removed under reduced pressure to give N-(n-hexyl) cyanoacetamide.

b. 1-(n-hexyl)-3-cyano-4,6-dimethylpyrid-2-one

To the above liquid is added 2,4-pentanedione (100 g., 1.0 mole), piperidine (10 ml.) and ethanol (300 ml.) and the mixture is refluxed with stirring for 4 hours. The ethanol is removed under reduced pressure, cooled in an ice bath and the resulting precipitate is collected by filtration to give 1-(n-hexyl)-3-cyano-4,6-dimethylpyrid-2-one, 22.3 g. 95.7% yield), mp. 63°–69° C.

c. 1-(n-hexyl)-3-carboxy-4,6-dimethylpyrid-2-one

To a stirred mixture of 1-(n-hexyl)-3-cyano-4,6-dimethyl-pyrid-2-one (222.3 g., 0.957 mole) and water (100 ml.) is added dropwise concentrated sulfuric acid (300 g.). When the addition is completed the stirred solution is heated on a steam bath for 24 hours. The solution is poured onto ice and basified with a sodium hydroxide solution and filtered. The alkaline filtrate is acidified with acetic acid and extracted with 400 ml. of toluene. The toluene layer is then extracted with 2 × 350 ml. of 5% NaOH. The aqueous layer is acidified with hydrochloric acid and cooled in an ice bath. The semi-solid precipitate is recrystallized from methanol/water to give 1-(n-hexyl)-3-carboxy-4,6-dimethylpyrid-2-one, 24 g. (100% yield), mp. 79–82.5.

Anal. Calc'd. for $C_{14}H_{21}NO_3$: C, 66.91; H, 8.42; N, 5.57. Found: C, 67.00; H, 8.42; N, 5.62.

EXAMPLE IV

Preparation of 1-(2-ethylhexyl)-3-carboxy-4,6-dimethylpyrid-2-one a. N-(2-ethylhexyl)cyanoacetamide.

To ethylcyanoacetate (141 g., 1.25 mole) is slowly added 2-ethylhexylamine (129 g., 1.0 mole) over a period of 0.5 hours. The solution is then gradually heated to 154° C. and the ethanol formed is collected over a period of 1.75 hours. The solution is then stripped of all volatiles boiling at or below 88° C./3.0 mm to give N-(2-ethylhexyl)cyanoacetamide, 201.5 g.

b. 1-(2-ethylhexyl)-3-cyano-4,6-dimethylpyrid-2-one

A mixture of N-(2-ethylhexyl)cyanoacetamide (201.5 g., 1.0 mole), 2,4-pentanedione (100 g., 1.0 mole), piperidine (10 g.) and 2-B-ethanol 300 ml. is refluxed for 24 hours, cooled to room temperature and the solid precipitate is collected by filtration to give 155 g. (60% yield), mp. 84°–89° C. The solid when recrystallized from petroleum ether/benzene has a mp. 89°–90° C.

Anal. Calc'd. for $C_{16}H_{24}N_2O$: C, 73.80; H, 9.29; N, 10.76. Found: C, 74.12; H, 9.23; N, 10.82.

c. 1-(2-ethylhexyl)-3-carboxy-4,6-dimethylpyrid-2-one

To concentrated sulfuric acid 450 ml. is added 1-(2-ethyl-hexyl)-3-cyano-4,6-dimethylpyrid-2-one (145 g., 0.56 mole) and then 140 g. of crushed ice is slowly added while maintaining the reaction temperature below 50° C. The reaction mixture is then heated on a steam bath for 24 hours. The cooled reaction mixture is poured onto 4 liters of crushed ice and the solid precipitate is removed by filtration. The solid is then triturated with dilute, aqueous sodium hydroxide, filtered, and the filtrate is acidified to pH 1. The resulting solid is then collected by filtration and air dried to give 130.5 g. (84%) of 1-(2-ethylhexyl)-3-carboxy-4,6-dimethylpyrid-2-one, mp. 89°–91° C.

Anal. Calc'd. for $C_{16}H_{25}NO_3$: C, 68.79; H, 9.02; N, 5.01. Found: C, 68.22; H, 9.23; N, 4.95.

EXAMPLE V

Preparation of 1(n-decyl)-3-carboxy-4,6-dimethylpyrid-2-one a. N-(n-decyl)cyanoacetamide To ethyl cyanoacetate (70.5 g., 0.625 mole) is slowly added n-decylamine (78.5 g., 0.500 mole) and the reaction mixture is slowly warmed to 150° C. while collecting the ethanol that distills from the reaction mixture. From the cooled reaction mixture crystallizes 77.3 g. of product, mp. 78.5°–81° C. The filtrate is further concentrated to give an additional 27 g. of N-(n-decyl)cyanoacetamide, mp. 78.5°–80.20 C. (total yield 93%).

Anal. Calc'd for $C_{13}H_{24}N_2O$: C, 69.60; H, 10.78; N, 12.49. Found: C, 69.88, H, 10.82; N, 12.40.

b. 1-(n-decyl)-3-cyano-4,6-dimethylpyrid-2-one

A mixture of N-(n-decyl)cyanoacetamide (93.4 g., 0.417 mole), 2.4-pentanedione (41.7 g., 0.417 mole), piperidine (8 ml.) and 2 B-ethanol (500 ml.) is stirred and refluxed for 17 hours. The mixture is cooled in an ice bath and the solid which crystallizes out is collected by filtration to give 1-(n-decyl)-3-cyano-4,6-dimethylpyrid-2-one, 95.2 g. mp. 82°–83° C.

Anal. Calc'd for $C_{18}H_{28}N_2O$: C, 74.95; H, 9.79; N, 9.71. Found: C, 74.67; H, 9.93; N, 9.61.

c. 1-(n-decyl)-3-carboxy-4,6-dimethylpyrid-2-one 1-(n-decyl)-3-cyano-4,6-dimethylpyrid-2-one (94.6 g., 0.33 mole) is dissolved in concentrated sulfuric acid (300 ml.) and crushed ice (90 g.) is slowly added while maintaining the reaction temperature below 75° C. The reaction mixture is then heated on a steam bath for 23 hours. The cooled reaction mixture is poured onto ice (700 g.) and the reaction mixture is diluted to 2300 ml. with water. The solid is collected by filtration and then triturated with dilute sodium hydroxide and filtered. The alkaline filtrate is acidified to pH 1 with concentrated hydrochloric acid. The resulting solid is collected by filtration and vacuum dried to give 1-(n-decyl)-3-carboxy-4,6-dimethylpyrid-2-one, 62.1 g. mp. 67.5°–72° C. The solid when recrystallized from methanol has a mp. of 74°–76.5° C.

Anal. Calc'd for $C_{18}H_{29}NO_3$: C, 70.32; H, 9.51; N, 4.56. Found: C, 69.98; H, 9.48; N, 4.81.

EXAMPLE VI

Preparation of 1-(2-ethylhexyl)-3-carboxypyrid-2-one a. 1-(2-ethylhexyl)-3-carboxypyrid-2-one ethyl ester Diethyl 2-(5-ethoxyallylidene) malonate (48.2 g., 0.20 mole), 2-ethylhexylamine (25.8 g., 0.20 mole) and imidazole (3.0 g.) are heated at 65° C. for 3.5 hours. The temperature is slowly raised to 185° C. over a period of 4.25 hours and the ethanol which is formed is removed by distillation. The solid which is obtained on cooling is dissolved in chloroform (300 ml.) and extracted first with 10% hydrochloric acid (50 ml.) and then with water (50 ml.). The chloroform layer is dried over sodium sulfate and evaporated to an oil. Recrystallization from ether/ethyl acetate gives 21.2% yield mp. 33°–40° C.

Anal. Calc'd for $C_{16}H_{25}NO_3$: C, 68.79; H, 9.02; N, 5.01. Found: C, 68.25; H, 9.01; N, 4.95.

b. 1-(2-ethylhexyl)-3-carboxypyrid-2-one

The ethyl ester is suspended in concentrated hydrochloric acid (200 ml.) and the mixture is refluxed for 1.5 hours. The reaction is cooled and poured into 300 ml. of ice water. The precipitate is collected and triturated with dilute sodium hydroxide overnight. Reacidification gives a 90% yield mp. 54°–6° C.

Anal. Calc'd for $C_{14}H_{21}NO_3$: C, 66.91; H, 8.42; N, 5.57. Found: C, 66.61; H, 7.98; N, 5.63.

EXAMPLE VII

Preparation of
1-(2-ethylhexyl)-3-carboxy-6-methyl-pyrid-2-one a. N-(2-ethylhexyl) cyanoacetamide The reaction is carried out as in IVa in a quantative yield.

b. 1-(2-ethylhexyl)-3-cyano-6-methylpyrid-2-one

N-(2-ethylhexyl) cyanoacetamide (60.4 g., 0.30 mole), 4-methoxy-3-butene-2-one (60.0 g., 0.60 mole), methyl-cello-solve (250 ml.) and 1,4-diazobicyclo [2.2.2.] octane (6.0 g.) are heated at reflux for 4 hours. Additional 4-methoxy-3-butene-2-one (30 g.) is added and reflux is continued for another 2 hours. The solvent is removed in vacuo to give an oil. The oil is dissolved in methylene chloride and extracted first with 2N—HCl (150 ml.) and then with water (2 × 250 ml.). The organic layer is dried over sodium sulfate, filtered and evaporated to dryness to give a 90% yield of crude product which is characterized by nmr and ir analysis.

c. 1-(2-ethylhexyl)-3-carboxy-6-methylpyrid-2-one

The above crude product is dissolved in conc. $H_2SO_4$ (40 ml.) and ice (12 g.) is added with cooling to keep temperature below 50° C. The reaction is then heated on a steam bath for 16 hours. The cooled reaction mixture is poured into ice water (400 ml.). The solid precipitate is collected and triturated with dilute sodium hydroxide. Reacidification gives a 59% yield, mp. 68°–71° C.

Anal. Calc'd for $C_{15}H_{23}NO_3$: C, 67.89; H, 8.73; N, 5.27 Found: C, 67.16; H, 8.56; N, 5.60.

Utilizing the above five examples and choosing the appropriate esters or ketones and N-alkyl acetamide the following compounds can be prepared.

1-methyl-3-carboxy-4,6-dimethylpyrid-2-one
1-isobutyl-3-carboxy-4,6-dimethylpyrid-2-one
1-(n-hexyl)-3-carboxy-4,6-dimethylpyrid-2-one
1-(2-ethylhexyl)-3-carboxy-4,6-dimethylpyrid-2-one
1-(n-decyl)-3-carboxy-4,6-dimethylpyrid-2-one
1-isopropyl-3-carboxypyrid-2-one
1-(t-butyl)-3-carboxypyrid-2-one
1-(n-heptyl)-3-carboxypyrid-2-one
1-(2-ethylhexyl)-3-carboxypyrid-2-one
1-(2-ethylhexyl)-3-carboxyl-6-methylpyrid-2-one
1-propyl-3-carboxy-6-methylpyrid-2-one
1-(butyl-3-carboxy-6-methylpyrid-2-one
1-isopentyl-3-carboxy-6-methylpyrid-2-one
1-(2-ethylhexyl)-3-carboxy-6-methylpyrid-2-one
1-(n-octyl)-3-carboxy-6-methylpyrid-2-one
1-(2-ethylnonyl)-3-carboxy-6-methylpyrid-2-one and salts thereof 1-methyl-3-cyano-4,6-dimethylpyrid-2-one
1-isobutyl-3-cyano-4,6-dimethylpyrid-2-one
1-(n-hexyl)-3-cyano-4.6-dimethypyrid-2-one
1-(2-ethylhexyl)-3-carbomethoxy-4,6-dimethylpyrid-2-one
1-(n-decyl)-3-carboethoxy-4,6-dimethylpyrid-2-one
1-methyl-3-carbamoyl-4,6-dimethylpyrid-2-one
1-isobutyl-3-carbamoyl-4,6-dimethylpyrid-2-one
1-(n-hexyl)-3-carbamoyl-4,6-dimethylpyrid-2-one
1-(2-ethylhexyl)-3-carbamoyl-4,6-dimethylpyrid-2-one
1-(n-decyl)-3-carbamoyl-4,6-dimethylpyrid-2-one.

The compounds of this invention have been found to produce a variety of plant growth regulatory responses. These responses are observed when the compounds alone or in a carrier or as formulations are applied to the plant itself, as by foliar application, or to plant parts such as by seed treatment or to the environment or habitat of the plant, such as by soil drenching or soil incorporation. The most outstanding plant growth influencing property is suppression of growth. This is most commonly found to be a growth inhibitory action on the stem, i.e., stem elongation is inhibited. In other instances flowering or seed formation is altered. In other cases malformation of leaves is noted. Sometimes particularly at high dosages, a plant species may be herbicidally sensitive.

Preemergence herbicical activity has also been obtained. Individual plant species give different types of responses and any one or several of these plant response may be observed for any given species. The major contribution of the compounds of this invention to the field of plant growth regulation is that they provide non-injurious plant growth regulants which inhibit stem elongation of many weed, crop and woody species and alter flowering and fruit development.

To obtain hybrid seed, the following procedure is generally employed. The two parents to be crossed are planted in alternate strips. The female parent is treated with a compound of the invention. The male-sterile female parent thus produced will be pollinated by pollen from the other, male-fertile, male parent, and the seed produced by the female parent will be hybrid seed which can then be harvested by conventional means.

A test is run to study gametocidal activity. For this test, the compound is applied as an aqueous solution to the plant in five different stages of growth from young seedlings up to and including the boot stage of development. Plants are sprayed to run-off with various dosage rates. When the plants reached the flowering stage of development, each spike or seed head is covered with a paper bag to prevent cross pollination. In those instances where the treatments delayed flowering the spikes are not covered with paper bags because viable pollen from the nonsprayed checks would no longer be available at these later dates. The most positive results are obtained with the plants in the boot stage.

No seed is produced in those spikes which are covered to prevent cross pollination. This absence of seeds indicate that fertilization has not taken place and that male sterility has been induced with the topical application of the sodium salt of the compounds. The presence of seed in a few treated seed heads that are not covered further indicates that cross pollination has occurred and the treatment has not affected the female portion of the spikelet. The higher dosage rates delays the time of flowering; thus, no pollen is available at this time for cross pollination since the non-treated check plants have flowered at an earlier date.

A soil drench test is used as one method for evaluating the plant growth regulating properties of the compounds of this invention. In this test, seeds or plants are planted in pots and at a given stage of growth the soil is watered with a preparation containing the compound at given dosages in terms of pounds per acre. Growth responses are subsequently observed.

For foliage spray tests, the compounds are dissolved in an appropriate solvent, usually acetone for the amides, acids and esters and water for the salts and sprayed onto the foliage at a given dosage per acre in a carrier volume of about 50 gallons per acre. Growth responses are subsequently observed.

In seed treatment tests an aqueous solution or suspension of the test compound is prepared and diluted to various percent concentrations. Seeds are then immersed in these preparations for about 20 hours, after which they are washed with water, planted in untreated soil, and the germination and growth is subsequently observed.

When the compounds of this invention are applied to plants or to the habitat of plants. they give a growth regulating response in the dosage range of about 0.01 to 30 pounds per acre (0.011 to 33 kilos per hectate). At the higher dosage, herbicidal responses can be manifested. Depending on the type of response desired the amount will vary with the plant species to be treated. Generally the preferred range is from 0.05 to 15 pounds per acre. Seeds can be treated with the compounds themselves or with any concentration of a solution of formulation of them.

The compounds of this invention can be employed as plant growth response agents either individually or as a mixture of two or more of them. They also can be used in combination with other plant growth regulatory compounds such as maleic hydrazide, succinic acid 2,2-dimethylhydrazide, choline and its salts, (2-chloroethyl)-trimethylammonium chloride, triiodobenzoic acid, tributyl-2,4-dichlorobenzylphosphonium chloride, polymeric N-vinyl-2-oxazolidiones, 1-(4-chlorophenyl)-3-carboxy-4,6-dimethylpyrid-2-one and its salts, tri(-dimethylaminoethyl)phosphate and its salts, and N-dimethylamino-1,2,3,6-tetrahydrophthalamic acid and its salts. The compounds of this invention can also be combined with a herbicide for use on plants which are not sensitive to the herbicide at weed controlling rates. For example, they can be combined with 2,4-D for use on monocotyledonous plants such as cereals and turf grasses, with 3'4'-dichloropropionanilide for use on rice or with 2,4-dichlorophenyl-4-nitrophenyl ether for use on rice and other cereals.

The compounds of this invention can be applied in liquid carriers. One preferred group of the compounds are the water soluble salts, in which case water is the preferred carrier. Nonphytotoxic organic solvents such as ketones, alcohols glycols, dimethylformamide and dimethyl sulfoxide can be employed. If desired, a surfactant such as a wetting agent can also be used and this usually constitutes a minor part (in general less than 10%) of the solution or formulation. The surface active agents can be anionic, cationic or non-ionic. For the water-soluble salts cationic and non-ionic surfactants are preferred. Commonly used surfactants are well known in the art and can be found in John W. McCutcheon, Inc., Morristown, N.J.

The compounds of this invention can be formulated in various ways as for example emulsifiable concentrates, wettable powders, dusts, granules and pellets. Usually for application to the plant or plant parts or the plant habitate, the formulations are extended with a suitable carrier. Emulsifiable concentrates are most usually extended with a liquid carrier such as water and dusts; granules and pellets are most usually extended with a solid carrier such as mineral clays.

Emulsifiable concentrates can be made by dissolving the compounds in an organic solvent and adding one or more solvent-soluble emulsifying agents. Suitable solvents are usually water-immiscible and can be found in the hydrocarbon, chlorinated hydrocarbon, ketone, ester, alcohol and amide classes of organic solvents.

Wettable powders can be made by incorporating the compounds in an inert, finely divided solid carrier along with a surfactant which can be one or more emulsifying, wetting, dispersing or spreading agents or blends of these. Suitable carriers can be found in the classes of clays, silicates, silicas, limes, carbonates and organic carriers.

Solid compositions in the form of dusts can be made by compounding the compounds of this invention with inert carriers conventionally employed for the manufacture of pesticidal dust for agricultural use, such as talcs, finely particled clays, pyrophyllite, diatomaceous earth, magnesium carbonate, wood or walnut shell flours.

Granular or pelletized formulations can be made by incorporating the compounds into granular or pelletized forms of agronomically acceptable carriers such as granular clays, vermiculite, charcoal, ground corncobs or bran.

The growth regulatory action of the compounds of the present invention can be advantageously employed in various ways. The production of shorter and thicker stems in cereal grains reduces the tendency toward lodging. Turf grasses can be maintained at a low height and the necessity for frequent mowing alleviated. The plant growth on embankments, such as roadsides, can be controlled to prevent erosion and at the same time maintain its aesthetic value. There can be an advantage in producing a dormant period in certain plants. The control of flowering and fruiting can be advantageous in the production of seedless fruit and for hybridization. Delaying the vegetative process or altering the time of flowering and fruiting can result in more advantageous harvest dates or increased flower, fruit and/or seed production. The chemical pruning of trees, shrubs, ornamentals and nursery stock can be beneficial. Other applications of the compounds of the present invention will suggest themselves to those skilled in the art of agriculture and horticulture.

We claim:
1. A compound of the formula

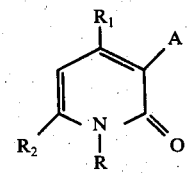

wherein
A is the group

wherein Y is halo, $NH_2$, OH, or $(C_1-C_7)$ alkoxy;

R is $(C_1-C_{12})$ alkyl, and $R_1$ and $R_2$ are methyl or ethyl and the physiologically acceptable salts thereof.

2. A compound according to claim 1 wherein A is carboxyl and the physiologically acceptable salts thereof.

3. A compound according to claim 2 wherein $R_1$ and $R_2$ are methyl and the physiologically acceptable salts thereof.

4. A compound according to claim 3 wherein R is n-hexyl and the physiologically acceptable salts thereof.

5. A method for producing gametocidal activity which comprises applying an effective amount of a compound of claim 1 to a plant, to plant seeds, or to the habitat of a plant.

6. A method for producing preemergence herbicidal activity which comprises applying an effective amount of a compound of claim 1 to the habitat of a plant.

7. A method for producing plant growth inhibition which comprises applying an effective amount of a compound of claim 1 to a plant, to plant seed, or to the habitat of a plant.

* * * * *